United States Patent [19]

Correia

[11] Patent Number: 5,414,116

[45] Date of Patent: May 9, 1995

[54] CATALYST FOR THE DEHALOGENATION OF ALPHAHALOGENATED CARBOXYLIC ACIDS AND ITS USE FOR PURIFYING MONOCHLOROACETIC ACID

[75] Inventor: Yves Correia, Chateau Arnoux, France

[73] Assignee: Societe Elf Atochem S.A., Puteaux, France

[21] Appl. No.: 20,944

[22] Filed: Feb. 19, 1993

[30] Foreign Application Priority Data

Feb. 19, 1992 [FR] France ................. 92 01876

[51] Int. Cl.$^6$ ............................. C07B 53/00
[52] U.S. Cl. ................... 562/606; 560/231; 560/236
[58] Field of Search ....................... 562/606

[56] References Cited

U.S. PATENT DOCUMENTS

| | | | |
|---|---|---|---|
| 3,829,478 | 8/1974 | Ohorodnirc | 562/604 |
| 3,864,281 | 2/1975 | Ohorodnirc | 502/262 |
| 3,901,660 | 8/1975 | Ohorodnirc | 23/288 |
| 5,191,118 | 3/1993 | Correia | 562/604 |

FOREIGN PATENT DOCUMENTS

| | | |
|---|---|---|
| 0453690 | 10/1991 | European Pat. Off. . |
| 2196196 | 3/1974 | France . |
| 2276876 | 1/1976 | France . |
| 2323777 | 6/1974 | Germany . |
| 1411214 | 10/1975 | United Kingdom . |
| 1503642 | 3/1978 | United Kingdom . |

*Primary Examiner*—Paul J. Killos
*Attorney, Agent, or Firm*—Morgan & Finnegan

[57] ABSTRACT

The invention relates to a catalyst formed of an active charcoal support in the form of particles or of cylinders having a diameter from 0.3 to 1.5 mm and a length of 0.3 to 5 mm or spheres having a diameter from 0.3 to 2 mm, the said particles being loaded with a precious metal from group 8. Advantageously, palladium on active charcoal is used.

The invention is particularly useful for purifying monochloroacetic acid.

5 Claims, No Drawings

CATALYST FOR THE DEHALOGENATION OF ALPHAHALOGENATED CARBOXYLIC ACIDS AND ITS USE FOR PURIFYING MONOCHLOROACETIC ACID

The present invention relates to a catalyst for the dehalogenation of alphahalogenated carboxylic acids and to its use for purifying monochloroacetic acid. It is particularly useful for removing dichloroacetic acid (DCAA) contained in monochloroacetic acid (MCAA). The synthesis of monochloroacetic acid on the industrial scale is carried out by chlorinating acetic acid, but dichloroacetic acid and sometimes a small amount of trichloroacetic are unavoidably formed. There is thus obtained, at the end of chlorination, a mixture consisting of monochloroacetic acid, dichloroacetic acid, traces of trichloroacetic acid and unreacted acetic acid. Taking into account the closeness of the boiling points of MCAA (189° C.) and DCAA (194° C.), it is practically impossible to separate them by distillation. On the other hand, it is very simple to hydrogenate this mixture in order to convert DCAA to MCAA according to the reaction:

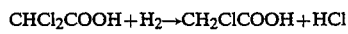

This hydrogenation is not entirely selective and a reversion of MCAA to acetic acid is also observed:

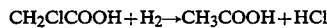

This reaction is carried out with a catalyst and byproduct of acetaldehyde which has the disadvantage of generating condensation products.

Patent FR 1,581,391 describes such a process in the liquid phase, based on a catalyst consisting of silica in the form of cylinders with a length of 8 mm and a diameter of 3.5 mm, having a palladium content of 0.5% by weight.

Patent FR 2,046,424 describes, in its Example 4, a catalyst for the purification of MCAA consisting of a silica powder with a size of 0.05 to 0.1 mm and loaded with palladium, the reaction being carried out in a fluidised bed in the liquid phase.

Patent GB 1,188,745 describes a catalyst made of silica in the form of cylinders with a length of 8 mm and a diameter of 3.5 mm for purifying MCAA in a stationary bed.

U.S. Pat. No. 2,863,917 also describes the purification of MCAA in the liquid phase by active charcoal in the powder form loaded with palladium in a stirred reactor.

Patent DE 1,915,037 describes the purification of MCAA by catalysts with a diameter of 5 mm in a stationary bed based on silica loaded with palladium and also silica powder with a size of 50 to 150 microns loaded with palladium in a stirred reactor.

Patent FR 2,027,078 also describes the purification of MCAA in the liquid phase in a stirred reactor in the presence of silica powder with a size of 40 to 200 microns, loaded with palladium.

U.S. Pat. No. 3,304,325 relates to the purification of MCAA in the vapour phase on active charcoal alone.

The Applicant has found a new catalyst which is useful for the dehalogenation of alphahalogenated carboxylic acids, which makes possible a more selective reaction which reduces by-products and greatly improves the productivity.

The present invention is thus a catalyst consisting essentially of an active charcoal support in the form of particles or cylinders having a diameter from 0.3 to 1.5 mm and a length of 0.3 to 5 mm or spheres having a diameter from 0.3 to 2 mm, the said particles being loaded with a precious metal from group 8 of the Periodic Table.

The precious metals from group VIII of the Periodic Table of the elements are ruthenium, rhodium, palladium, osmium, iridium and platinum. Advantageously the first three and preferably palladium are used. These metals can be used on their own, as alloys or as mixtures with each other.

The precious metal is deposited on an active charcoal, that is to say a charcoal with a large specific surface, at a level of 0.3 to 1% by weight of the catalyst, that is to say of the charcoal plus metal, and it is distributed on the surface of the charcoal. Charcoal with a large specific surface means a charcoal with a specific surface of approximately 600 m²/g and which can range up to 1,300 m²/g.

More simply, the size of the particles can also be translated into the number of particles of a diameter per cm³, when these particles are in bulk in a receptacle.

It would not be departing from the scope of the invention if a small portion of the catalyst was made of particles outside the range 0.3-2 mm, for example 5 to 15 % by weight of the entire catalyst.

Advantageously, the catalyst of the invention consists of particles with a size of between 0.7 and 1.2 mm, in diameter, whether they be cylindrical or spherical. This catalyst can be entirely or partly doped with sulphur or sulphur compounds, as described in EP 0,453,690. The advantages of these catalysts are described later in the process.

The present invention also relates to the use of these catalysts, that is to say to a process for the dehalogenation of alphahalogenated carboxylic acids.

The present invention is thus a process for the dehalogenation of alphahalogenated carboxylic acids or of their esters by hydrogen, characterised in that the dehalogenation is carried out in the presence of the catalyst which has just been described.

The invention is particularly useful for the acids of formula:

in which X is chlorine or bromine, $R_1$ and $R_2$ are identical or different and represent chlorine, bromine, H, a linear or branched alkyl radical having from 1 to 12 carbon atoms or a cycloalkyl radical having from 3 to 12 carbon atoms. The invention also applies to the esters of the acids of formula (I). These are preferably aliphatic esters having from 1 to 10 carbon atoms, and preferably 1 to 5 carbon atoms.

According to the invention, the dehalogenation of an acid or of a mixture of acids can be carried out. These acids can also be mixed with a solvent.

Depending on the applications of the dehalogenated acids, it is sometimes necessary to separate the catalyst from the acids at the end of dehalogenation. According to an advantageous form of the invention, the catalyst is arranged in a stationary bed or in a fluidised bed in a container and the acids to be dehalogenated and hydrogen are introduced into this container. It is therefore unnecessary to separate the catalyst at the end of dehalogenation. Preferably, a catalyst in a stationary bed is used and the dehalogenation is carried out continuously.

It is advantageous to carry out the process of the invention with the acids in the liquid phase. Although it is possible to carry out the dehalogenation at any temperature, it is advantageous to be between the temperature at which the acids are liquid and 200° C., and preferably between 100 and 180° C. If necessary, the acid(s) can be put in a solvent in order to be able to be within this preferred temperature region.

The dehalogenation can be carried out at atmospheric pressure or up to 5 bars. The effect of the pressure is to increase the reaction kinetics, as the acids as well as the reaction mixture of the invention are corrosive, it is not prudent to exceed a pressure of the order of 5 bars.

The invention is particularly useful for purifying impure monoalphahalogenated carboxylic acids $R_1CHXCOOH$, $R_1$ having the above meaning. These acids are prepared by halogenating the corresponding acid $R_1CH_2COOH$, and a mixture is obtained of $R_1CHXCOOH$, $R_1CX_2COOH$, unconverted acid $R_1CH_2COOH$ and sometimes traces of $CX_3COOH$ in the specific case of the acid $CH_3COOH$.

$R_1CH_2COOH$ could first be separated from this mixture but it is simpler first to hydrogenate $$R_1CX_2COOH + H_2 \rightarrow R_1CHXCOOH + HX$$

and then to separate, since a part unavoidably reverts to acid according to $$R_1CHXCOOH + H_2 \rightarrow R_1CH_2COOH + HX$$

It is then sufficient to distil the mixture of $R_1CHXCOOH$, $R_1CH_2COOH$ and HX in order to obtain relatively pure $R_1CHXCOOH$. During hydrogenation, aldehydes, for example $R_1CH_2CHO$, are formed.

The reversion is the ratio between the number of $X^-$ ions in the purified acid, that is to say those arising from HX, and the theoretical number of X to be removed from $R_1CX_2COOH$ (and possibly $CX_3COOH$) in order to convert it to $R_1CHXCOOH$. With the exception of $CX_3COOH$, the minimum reversion is 1. This reversion is most often between 1.4 and 3.4.

The catalyst of the invention makes it possible to lower the amount of aldehydes and to improve the reversion, while using the same amount of palladium.

The size of the catalyst of the invention makes it possible for the dehalogenation to be carried out in a stationary bed without an awkward pressure drop.

The present invention also relates to a process in which the catalyst of the invention is used in series with a catalyst of larger size.

This catalyst of larger size is a support made of active charcoal in the form of particles loaded with precious metal from group 8. The large size can be defined by cylinders with a diameter greater than 2 mm and a length greater than 3 mm and by spheres with a diameter greater than 3 mm. It is sufficient that 85 to 95% by weight of a catalyst charge has these dimensions for it to be "of larger size" within the meaning of the invention.

A hydrogen stream can be used which is co-current or countercurrent with the acid stream.

EXAMPLE 1

In a plant consisting of two tubular glass reactors, with an internal diameter of 26 mm and a volume of 300 $cm^3$ heated by double jackets and equipped with equipment which makes it possible to supply, at co- or countercurrent, monochloroacetic acid to be purified and hydrogen at perfectly regular flow rates, there is placed, in one of the reactors A, a catalyst consisting of active charcoal grains impregnated with 0.8% palladium, 17.25 grains to the $cm^3$ and a specific surface in the region of 1,200 $m^2/g$ and having a density of 0.433 $g/cm^3$.

A catalyst of the same relative density, specific surface, density and palladium content, but consisting of 408 grains to the $cm^3$ that is to say that Catalysts A and B contain the same amount of palladium, is placed in Reactor B. The system is then put into operation in the countercurrent mode, seeking a residual dichloroacetic acid content of less than 0.2%. For this, the temperature is varied. The flow rates of liquid, gas and hydrogen remain constant.

Monochloroacetic acid to be purified (weight %):

| | |
|---|---|
| Monochloroacetic acid (MCAA): | 80 |
| Dichloroacetic acid (DCAA): | 4 |
| Acetic acid: | 16 |
| Catalyst A has the size | Diameter 3 mm |
| | Length 10 mm |
| Catalyst B has the size | Diameter 1 mm |
| | Length 3 mm |

Table I below, consisting of two operational schedules of the system, shows that the finer catalyst makes it possible to work at a lower temperature and generates fewer by-products.

TABLE I

| | Temperature (°C.) | Spatial Rate (Kg/h/m³) | Residual DCAA (%) | GAMA Content (%) | Aldehydes generated (mg/Kg) | Reversion |
|---|---|---|---|---|---|---|
| 1A Reactor A | 125 | 245 | 0.15 | 0.46 | 850 | 2.47 |
| 2A Reactor A | 140 | 465 | 0.07 | 0.6 | 723 | 2,89 |
| 3A Reactor A | 140 | 475 | 0.12 | 0.50 | 1170 | 2.54 |
| 1B Reactor B | 110 | 250 | 0.10 | ≦0.09 | 490 | 2.3 |
| 2B Reactor | 115 | 494 | 0.09 | ≦0.05 | 413 | 1.83 |

TABLE I-continued

| | Temperature (°C.) | Spatial Rate (Kg/h/m³) | Residual DCAA (%) | GAMA Content (%) | Aldehydes generated (mg/Kg) | Reversion |
|---|---|---|---|---|---|---|
| B | | | | | | |
| 3B Reactor B | 120 | 823 | 0.17 | ≦0.05 | 550 | 2.1 |

Reversion = ratio between the total chlorides and the chlorides arising from the reduction of DCAA to MCAA.
The aldehydes are expressed as acetaldehyde.

In Table I:
Items of information 1A and 1B show the values at identical times.
The temperature in the column is the temperature read by a thermocouple in the catalyst bed.
The spatial rate is in kg of crude acid per hour and volume of catalyst bed.
The GAMA (glycolic acid monochloroacetate) content is at the reactor outlet in the purified acid.

EXAMPLE 2

The two reactors of Example 1 containing the same catalysts are arranged in series in order to purify MCAA of the same composition as in Example 1.

2.1. Crude MCAA first passes over the catalyst of small size (Results in Table II). The operating temperature was sought which would give a final DCAA content less than or equal to 0.2%. The following measurements were carried out between the 225th and 346th hour of operation.

TABLE II

| | Example 2.1 | Example 2.2 |
|---|---|---|
| Spatial rate (crude MCAA) | 250 kg/h.m³ | 250 kg/h.m³ |
| Catalyst temperature (in both reactors) | 115° C. | 115° C. |
| DCAA at the outlet of the 1st reactor | 0.25 to 0.33 | 1.1 to 1.2 |
| DCAA at the outlet of the 2nd reactor | 0.10 to 0.13 | 0.07 to 0.11 |
| Acetaldehyde generated (mg/kg of acid) | 120 to 140 | 85 to 89 |

2.2. MCAA first passes over the catalyst of large size. The temperature is kept at 115° C. A very significant gain in aldehyde with respect to Example 1 is observed.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. Process for the dehalogenation or alphahalogenated carboxylic acids and their esters by hydrogen, comprising carrying out the dehalogenation in the presence of a catalyst consisting essentially of an active charcoal support in the form of particles or cylinders having a diameter from 0.3 to 1.5 mm and a length of about 0.3 to 5 mm or spheres having a diameter from 0.3 to 2 mm, the said particles being loaded with a precious metal from group VIII of the Periodic Table of Elements.

2. Process according to claim 1, characterised wherein the acids are of formula $R_1CHXCOOH$ in which X represents chlorine or bromine, $R_1$ represents chlorine, bromine, H or a linear or branched alkyl radical having from 1 to 12 carbon atoms or a cycloalkyl radical having from 3 to 13 carbon atoms.

3. Process according to claim 1, wherein the acids are in the liquid phase.

4. Process according to claim 2, wherein the acids are in the liquids phase.

5. Process for the dehalogenation of alphahalogenated carboxylic acids and their esters by hydrogen, comprising the steps of:
carrying out the dehalogenation in the presence of a catalyst consisting essentially of an active charcoal support in the form of particles or cylinders having a diameter from 0.3 to 1.5 mm and a length of about 0.3 to 5 mm or spheres having a diameter from 0.3 to 2 mm, the said particles being loaded with a precious metal from group VIII of the Periodic Table of Elements;
passing said alphahalogenated carboxylic acid and their esters by a second catalyst in series wherein said second catalyst is of a greater size than said catalyst.

* * * * *